United States Patent
Takabayashi et al.

(10) Patent No.: US 9,687,264 B2
(45) Date of Patent: Jun. 27, 2017

(54) GRASPING TREATMENT DEVICE

(71) Applicant: OLYMPUS CORPORATION, Tokyo (JP)

(72) Inventors: Junichi Takabayashi, Kokubunji (JP); Shinya Masuda, Hino (JP); Eiji Murakami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/939,685

(22) Filed: Jul. 11, 2013

(65) Prior Publication Data

US 2014/0031809 A1 Jan. 30, 2014

Related U.S. Application Data

(63) Continuation of application No. PCT/JP2013/051329, filed on Jan. 23, 2013.
(Continued)

(51) Int. Cl.
*A61B 17/32* (2006.01)
*A61B 18/18* (2006.01)
(Continued)

(52) U.S. Cl.
CPC .. *A61B 17/320092* (2013.01); *A61B 18/1445* (2013.01); *A61B 18/18* (2013.01);
(Continued)

(58) Field of Classification Search
CPC ........ A61B 17/320092; A61B 18/1445; A61B 2018/1452
(Continued)

(56) References Cited

U.S. PATENT DOCUMENTS 6,063,050 A * 5/2000 Manna et al. .................. 604/22
6,068,647 A * 5/2000 Witt et al. ...................... 606/205
(Continued)

FOREIGN PATENT DOCUMENTS

CN 101370440 A 2/2009
EP 1 327 420 A1 7/2003
(Continued)

OTHER PUBLICATIONS

International Search Report issued in Application No. PCT/JP2013/051329; Dated Apr. 16, 2013 (With Translation).
(Continued)

*Primary Examiner* — Ronald Hupczey, Jr.
(74) *Attorney, Agent, or Firm* — Oliff PLC

(57) ABSTRACT

A jaw of the grasping treatment device includes an abutting portion being abutable on a probe treatment portion when the jaw is closed relative to the probe treatment portion, and a separated portion being disposed with a clearance between the separated portion and the probe treatment portion when the abutting portion is in abutment with the probe treatment portion. The jaw includes a distal-side wall portion provided to a distal direction side of the separated portion and protruding toward the probe treatment portion as compared with the separated portion, and a proximal-side wall portion provided to a proximal direction side of the separated portion and which protruding toward the probe treatment portion as compared with the separated portion.

8 Claims, 10 Drawing Sheets

Related U.S. Application Data

(60) Provisional application No. 61/593,606, filed on Feb. 1, 2012.

(51) Int. Cl.
*A61B 18/14* (2006.01)
*A61B 18/00* (2006.01)

(52) U.S. Cl.
CPC ............ *A61B 2018/0063* (2013.01); *A61B 2018/00345* (2013.01); *A61B 2018/00494* (2013.01); *A61B 2018/00607* (2013.01); *A61B 2018/00994* (2013.01)

(58) Field of Classification Search
USPC .................... 606/50–52, 205–207, 169
See application file for complete search history.

(56) References Cited

U.S. PATENT DOCUMENTS

| | | | |
|---|---|---|---|
| 6,569,178 B1 * | 5/2003 | Miyawaki et al. | 606/169 |
| 6,669,690 B1 * | 12/2003 | Okada et al. | 606/40 |
| 2003/0114874 A1 | 6/2003 | Craig et al. | |
| 2004/0078035 A1 | 4/2004 | Kanehira et al. | |
| 2005/0234338 A1 | 10/2005 | Masuda | |
| 2007/0198005 A1 | 8/2007 | Ichihashi et al. | |
| 2009/0088668 A1 * | 4/2009 | Masuda | A61B 17/320092 601/2 |
| 2009/0088743 A1 | 4/2009 | Masuda | |
| 2009/0143806 A1 | 6/2009 | Witt et al. | |
| 2009/0216157 A1 | 8/2009 | Yamada | |

FOREIGN PATENT DOCUMENTS

| | | |
|---|---|---|
| EP | 2 105 100 A1 | 9/2009 |
| JP | A-2000-312682 | 11/2000 |
| JP | A-2001-340349 | 12/2001 |
| JP | 2004-242959 A | 9/2004 |
| JP | A-2009-195676 | 9/2009 |
| JP | A-2011-505198 | 2/2011 |
| WO | WO 2007/097330 A1 | 8/2007 |
| WO | WO 2011/099571 A1 | 8/2011 |

OTHER PUBLICATIONS

Aug. 14, 2014 International Preliminary Report on Patentability issued in International Patent Application No. PCT/JP2013/051329.

May 13, 2015 Search Report in European Patent Application No. 13743928.7.

Sep. 6, 2015 Office Action issued in Chinese Patent Application No. 201380002430.0.

Apr. 27, 2016 Office Action issued in Chinese Patent Application No. 201380002430.0.

Oct. 21, 2016 Office Action issued in Chinese Applicaiton No. 201380002430.0.

* cited by examiner

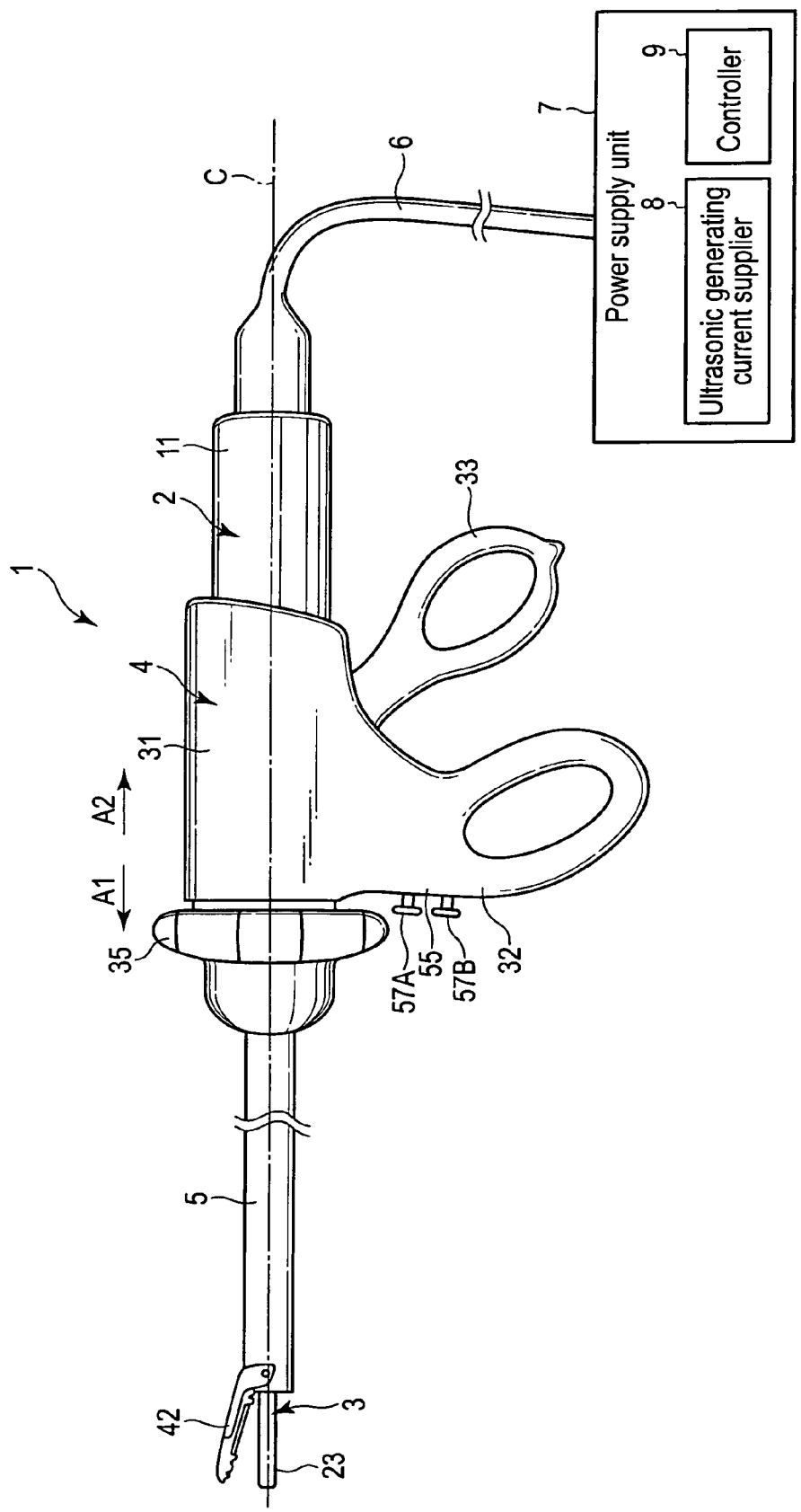
F I G. 1

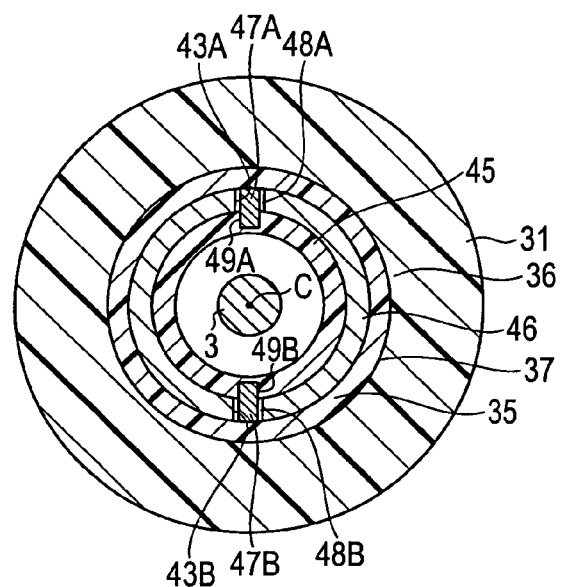
F I G. 5
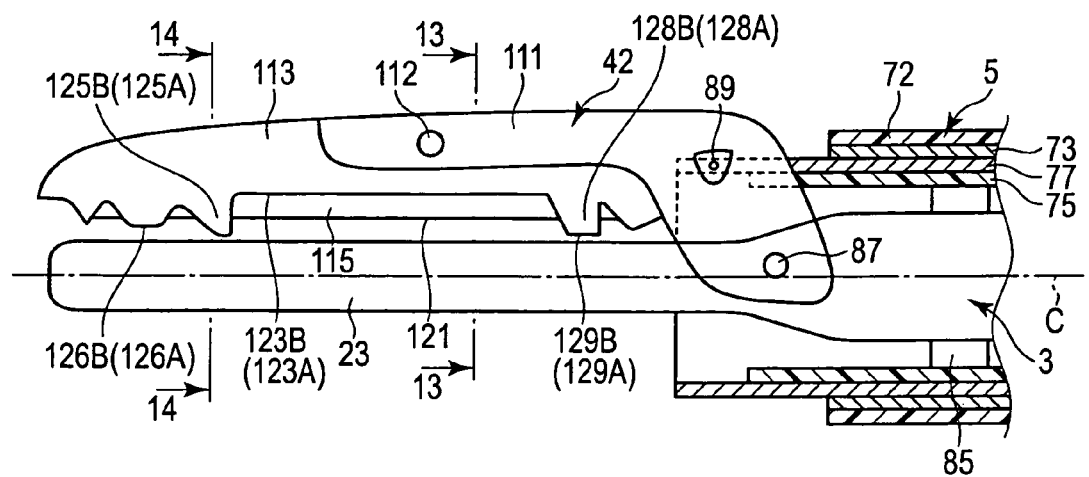
F I G. 6

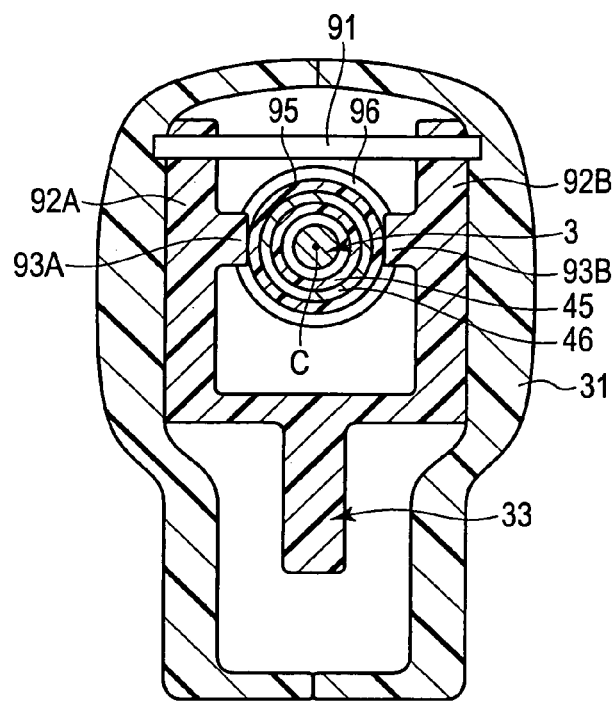
F I G. 7
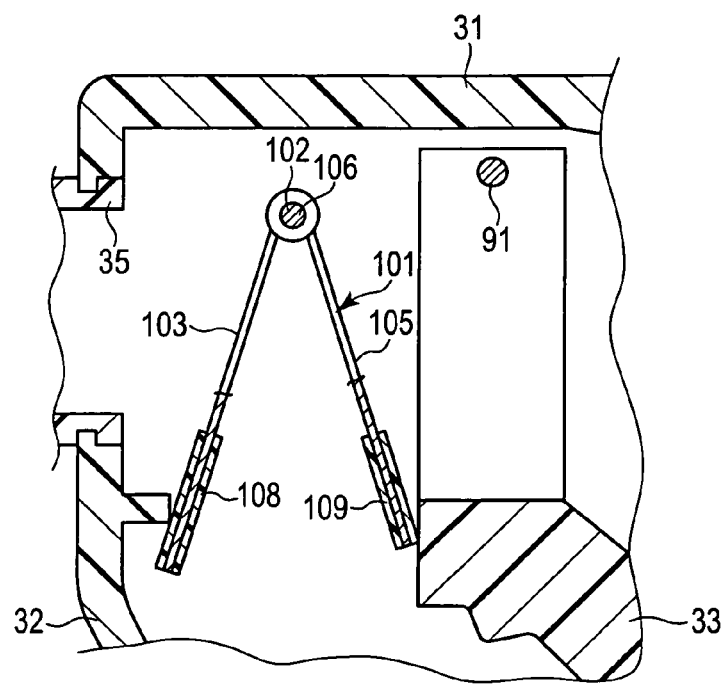
F I G. 8

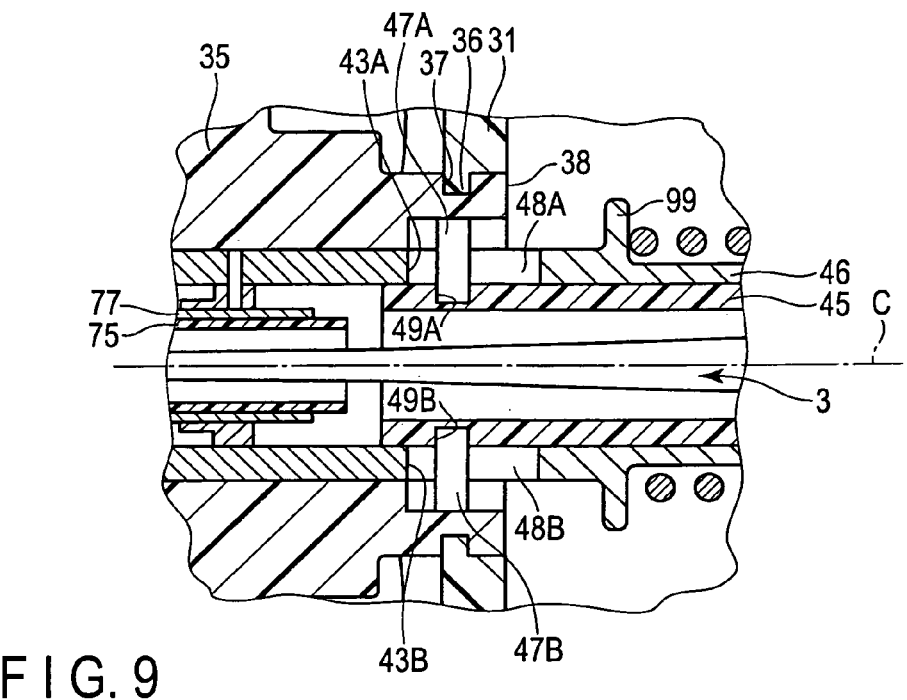
F I G. 9
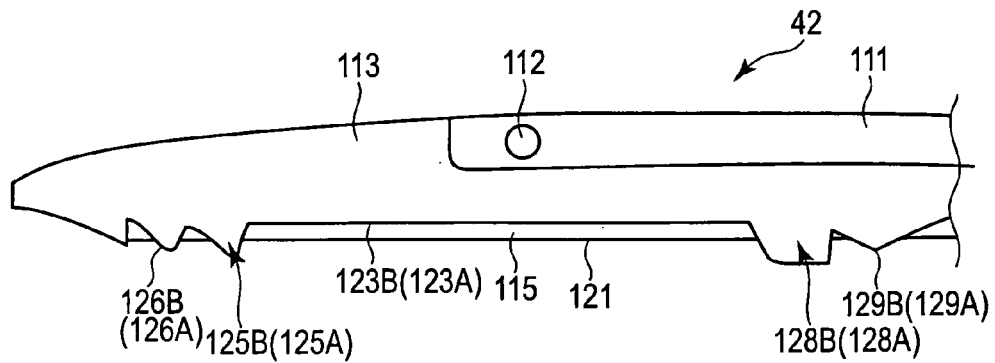
F I G. 10
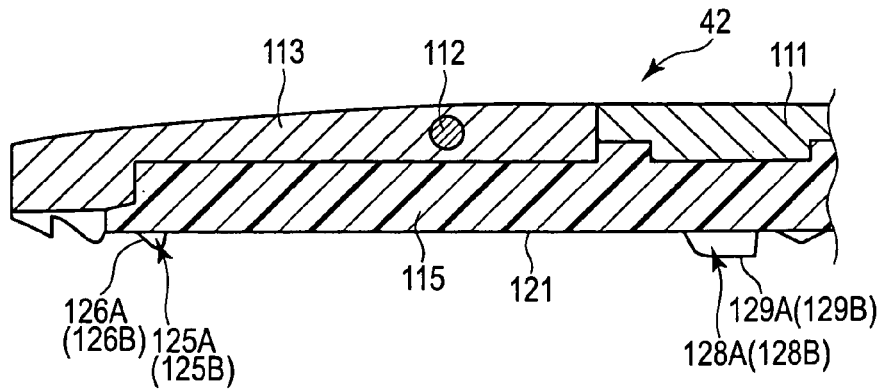
F I G. 11

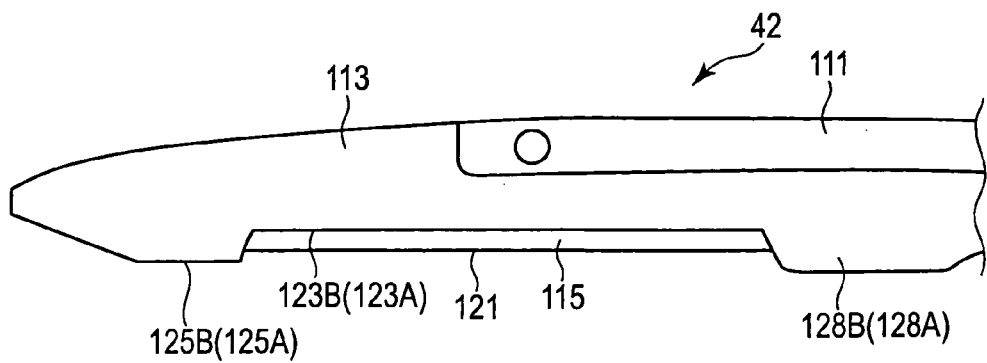
F I G. 18
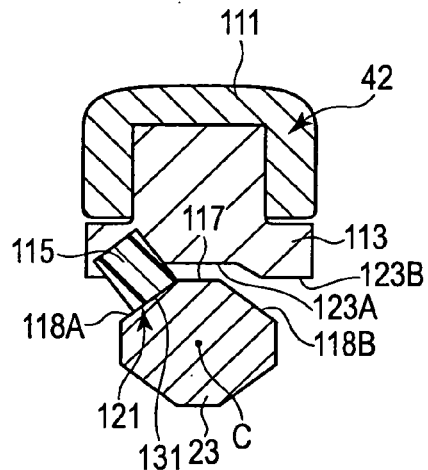
F I G. 19
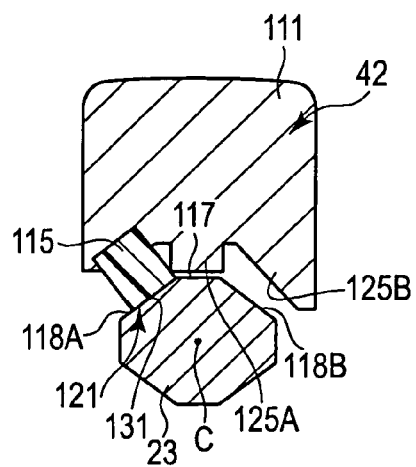
F I G. 20

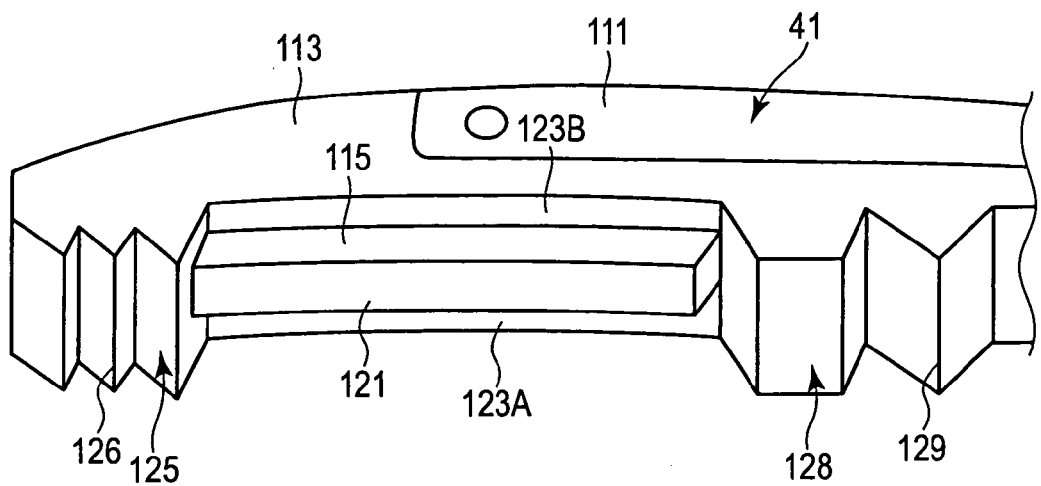
F I G. 21
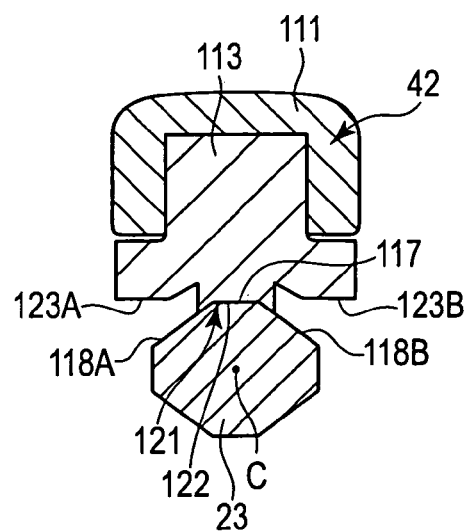
F I G. 22

GRASPING TREATMENT DEVICE

CROSS-REFERENCE TO RELATED APPLICATIONS

This is a Continuation Application of PCT Application No. PCT/JP2013/051329, filed Jan. 23, 2013 and based upon and claiming the benefit of priority from prior U.S. Provisional Application No. 61/593,606, filed Feb. 1, 2012, the entire contents of which are incorporated herein by reference.

BACKGROUND OF THE INVENTION

1. Field of the Invention

The present invention relates to a grasping treatment device. The grasping treatment device is configured to grasp a grasping target such as a living tissue between a probe treatment portion provided in a distal portion of a probe and a jaw configured to open or close relative to the probe treatment portion. The grasping treatment device uses energy such as ultrasonic vibrations or a high-frequency current to conduct (perform) a treatment.

2. Description of the Related Art

Jpn. Pat. Appln. KOKAI Publication No. 2001-340349 has disclosed a grasping treatment device configured to grasp a grasping target such as a living tissue between a probe treatment portion provided in a distal portion of a probe and a jaw. In this grasping treatment device, heaters are respectively attached to the probe treatment portion and the jaw. The heater of the probe treatment portion and the heater of the jaw are formed into a planar shape having a surface that is not uneven. Heat generated by the heaters is used in cutting and coagulation of the grasping target (living tissue) grasped between the heater of the probe treatment portion and the heater of the jaw. The probe treatment portion includes a tooth portion provided to a distal direction side of the heater, and a surface of the tooth portion that faces the jaw is formed into an uneven shape along a longitudinal axis. The jaw includes a tooth portion provided to the distal direction side of the heater, and a surface of the tooth portion that faces the probe treatment portion is formed into an uneven shape along the longitudinal axis.

BRIEF SUMMARY OF THE INVENTION

According to one aspect of the invention, a grasping treatment device includes that a probe extended along a longitudinal axis, the probe including a probe treatment portion provided to a distal portion thereof; a jaw which is configured to open or close relative to the probe treatment portion, and which is configured to grasp a grasping target between the probe treatment portion and the jaw; an abutting portion which is provided to the jaw, and which is configured to be abutable on the probe treatment portion when the jaw is closed relative to the probe treatment portion; a separated portion which is provided to the jaw, and which is configured to be disposed with a clearance between the separated portion and the probe treatment portion when the abutting portion is in abutment with the probe treatment portion; a distal-side wall portion which is provided to a distal direction side of the separated portion in the jaw, and which protrudes toward the probe treatment portion as compared with the separated portion, the distal-side wall portion being configured to regulate a movement of the grasping target toward the distal direction away from the separated portion; and a proximal-side wall portion which is provided to a proximal direction side of the separated portion in the jaw, and which protrudes toward the probe treatment portion as compared with the separated portion, the proximal-side wall portion being configured to regulate a movement of the grasping target toward the proximal direction away from the separated portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a grasping treatment device according to a first embodiment of the present invention;

FIG. 5 is a sectional view taken along the line V-V in FIG. 4;

FIG. 6 is a partly sectional schematic view showing the configurations of a distal portion of the probe, a distal portion of the sheath, and a jaw according to the first embodiment;

FIG. 7 is a sectional view taken along the line VII-VII in FIG. 4;

FIG. 8 is a schematic sectional view showing the configuration of attaching a torsion spring to the handle unit according to the first embodiment;

FIG. 9 is a schematic sectional view showing the configuration of coupling a rotational operation knob to a movable cylindrical member when a protrusion of a movable handle is in abutment with an abutting portion of a cylindrical case according to the first embodiment;

FIG. 10 is a schematic side view showing the configuration of the jaw according to the first embodiment;

FIG. 11 is a schematic sectional view showing the configuration of the jaw according to the first embodiment;

FIG. 18 is a schematic side view showing the jaw according to a first modification;

FIG. 19 is a schematic sectional view showing sections of the jaw and the probe treatment portion which are perpendicular to a longitudinal axis and which pass through separated portions according to a second modification;

FIG. 20 is a schematic sectional view showing sections of the jaw and the probe treatment portion which are perpendicular to the longitudinal axis and which pass through distal-side wall portions according to the second modification;

FIG. 21 is a schematic perspective view showing the jaw according to a third modification; and FIG. 22 is a schematic sectional view showing sections of the jaw and the probe treatment portion which are perpendicular to the longitudinal axis and which pass through the separated portions according to a fourth modification.

DETAILED DESCRIPTION OF THE INVENTION

First Embodiment

Figure 2:
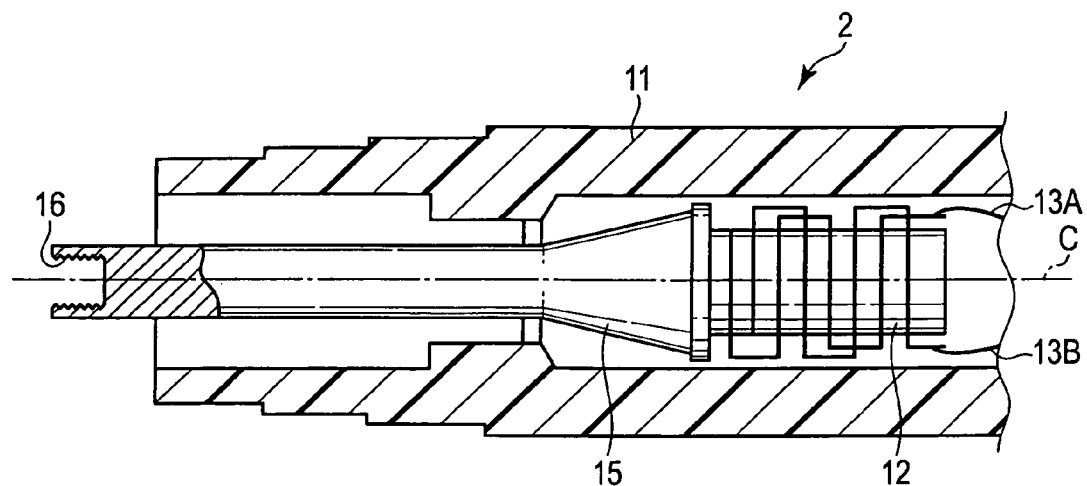
FIG. 2 is a schematic sectional view showing the configuration of a vibrator unit according to the first embodiment.

A first embodiment of the present invention is described with reference to FIG. 1 to FIG. 17. FIG. 1 is a diagram showing a grasping treatment device (grasping surgical device) 1 according to the present embodiment. As shown in FIG. 1, the grasping treatment device 1 has a longitudinal axis C. Here, one of two directions parallel to the longitudinal axis C is a distal direction (direction of an arrow A1 in FIG. 1), and a direction opposite to the distal direction is a proximal direction (direction of an arrow A2 in FIG. 1).

The grasping treatment device 1 includes a vibrator unit (oscillator unit) 2, a probe 3, a handle unit 4, and a sheath 5. The vibrator unit 2 includes a vibrator case 11. One end of a cable 6 is connected to a proximal end of the vibrator case 11. The other end of the cable 6 is connected to a power supply unit 7. The power supply unit 7 includes an ultrasonic generating current supplier 8, and a controller 9.

FIG. 2 is a diagram showing the configuration of the vibrator unit 2. As shown in FIG. 2, an ultrasonic vibrator 12 which includes piezoelectric elements configured to convert a current to ultrasonic vibrations is provided in the vibrator case 11. One end of each of electric signal lines 13A and 13B is connected to the ultrasonic vibrator 12. Each of the electric signal lines 13A and 13B has the other end connected to the ultrasonic generating current supplier 8 of the power supply unit 7 through an inside of the cable 6. Ultrasonic vibrations are generated in the ultrasonic vibrator 12 by the supply of a current to the ultrasonic vibrator 12 from the ultrasonic generating current supplier 8 via the electric signal lines 13A and 13B. A columnar horn 15 configured to increase the amplitude of the ultrasonic vibrations is coupled to the distal direction side of the ultrasonic vibrator 12. The horn 15 is supported by the vibrator case 11. An internal thread 16 is formed in a distal portion of the horn 15.

Figure 3:
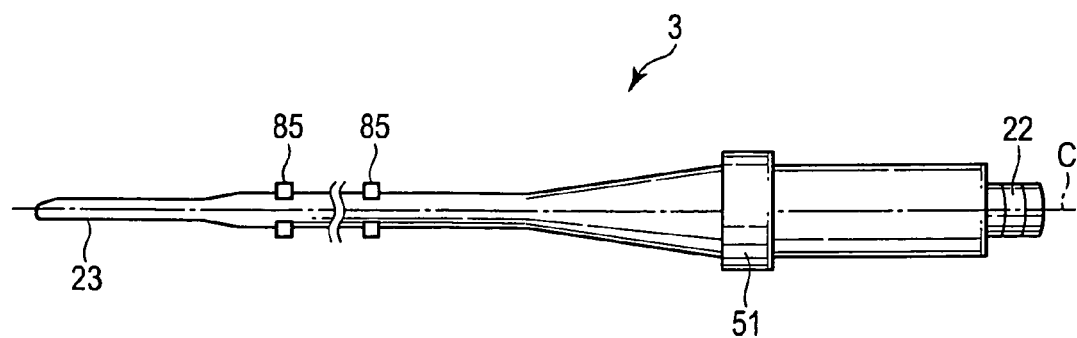
FIG. 3 is a schematic side view showing the configuration of a probe according to the first embodiment.

FIG. 3 is a diagram showing the configuration of the probe 3. As shown in FIG. 3, the probe 3 is formed into a columnar shape along the longitudinal axis C. The longitudinal axis C of the grasping treatment device 1 passes through an axial center of the probe 3. An external thread 22 is provided to a proximal direction side part of the probe 3.

When the external thread 22 of the probe 3 is screwed to the internal thread 16 of horn 15, the ultrasonic probe 3 is attached to the horn 15.

When the probe 3 is attached to the horn 15, the ultrasonic vibrations generated in the ultrasonic vibrator 12 can be transmitted to a distal portion of the ultrasonic probe 3 via the horn 15. That is, the probe 3 configured to transmit the ultrasonic vibrations from the proximal direction to the distal direction. The probe 3 is an ultrasonic probe configured to be vibrated in directions parallel to the longitudinal axis C by the ultrasonic vibrations. A probe treatment portion 23 as a treatment portion is provided to the distal portion of the probe 3.

As shown in FIG. 1, the handle unit 4 includes a cylindrical case 31 extending along the longitudinal axis C. The cylindrical case 31 is made of an insulating material. A fixed handle 32 extends from the cylindrical case 31 toward one of directions perpendicular to the longitudinal axis C. The fixed handle 32 is formed integrally with the cylindrical case 31. A movable handle 33 is rotatably attached to the cylindrical case 31. The movable handle 33 is configured to open or close relative to the fixed handle 32 substantially parallel with respect to the longitudinal axis C. The movable handle 33 is located to the proximal direction side of the fixed handle 32.

The vibrator unit 2 is coupled to the cylindrical case 31 from the proximal direction side, and the sheath 5 is coupled to the cylindrical case 31 from the distal direction side. The probe 3 is inserted into the cylindrical case 31 from the distal direction side, and the probe 3 is inserted through the sheath 5. A jaw 42 is rotatably attached to a distal portion of the sheath 5. The jaw 42 is configured to open or close relative to the probe treatment portion 23 of the probe 3. An operation of opening or closing the jaw 42 relative to the probe treatment portion 23 is performed by the movable handle 33 which is an open-and-close operation input section.

The handle unit 4 also includes a rotational operation knob 35 which is a rotational operation input section coupled to the distal direction side of the cylindrical case 31. The rotational operation knob 35 is coupled to the cylindrical case 31 rotatably in directions around the longitudinal axis. When the rotational operation knob 35 rotates relative to the cylindrical case 31, the vibrator unit 2, the probe 3, the sheath 5, and the jaw 42 rotate relative to the cylindrical case 31 in one of the directions around the longitudinal axis.

Figure 4:
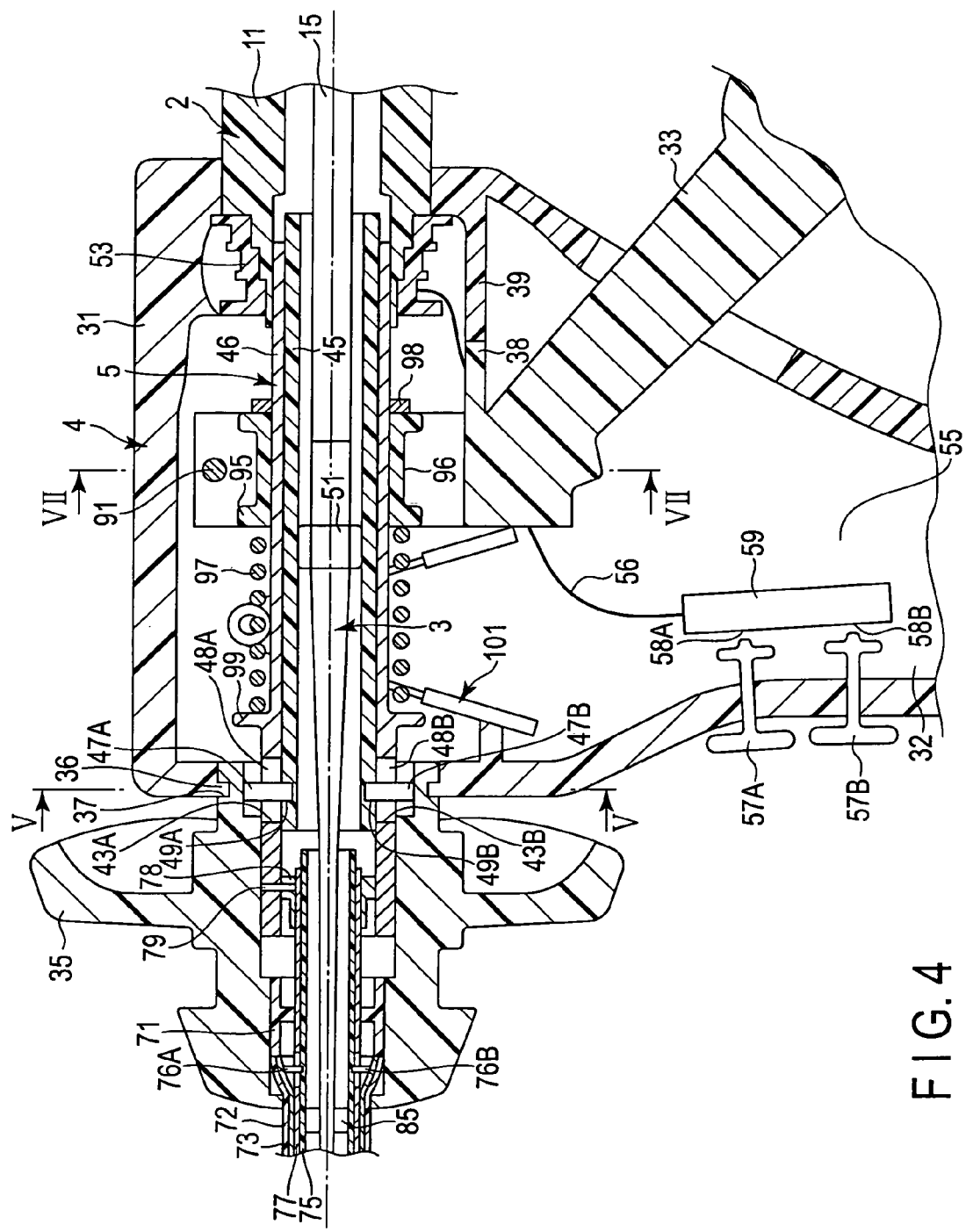
FIG. 4 is a schematic sectional view showing the internal configuration of a handle unit according to the first embodiment.

FIG. 4 is a diagram showing the internal configuration of the handle unit 4. As shown in FIG. 4, an engaging protrusion 36 protruding toward an inner peripheral direction is provided in the cylindrical case 31. The engaging protrusion 36 is provided to all-round circumference in the directions around the longitudinal axis. An engaging groove 37 which engages with the engaging protrusion 36 is provided in the rotational operation knob 35. The engaging groove 37 is provided to all-round circumference in the directions around the longitudinal axis. The engaging protrusion 36 and the engaging groove 37 engage movably relative to each other in the directions around the longitudinal axis. Thus, the rotational operation knob 35 is attached to the cylindrical case 31 rotatably in the directions around the longitudinal axis.

The probe 3 and the sheath 5 extend up to an inside of the cylindrical case 31 along the longitudinal axis C through an inside of the rotational operation knob 35. A proximal end of the probe 3 is attached to the horn 15 inside the cylindrical case 31. As a result, the vibrator unit 2 is coupled to the probe 3. A proximal portion of the sheath 5 is coupled to the vibrator case 11 inside the cylindrical case 31. As a result, the vibrator unit 2 is coupled to the sheath 5.

A connection cylindrical member 45 which couples the probe 3 to the sheath 5 is provided inside the cylindrical case 31 of the handle unit 4. The sheath 5 includes a movable cylindrical member 46 provided to an outer peripheral direction side of the connection cylindrical member 45. The connection cylindrical member 45 and the movable cylindrical member 46 are provided along the longitudinal axis C.

FIG. 5 is a sectional view taken along the line V-V in FIG. 4. As shown in FIG. 4 and FIG. 5, engaging pins 47A and 47B are fixed to the rotational operation knob 35 so that these engaging pins 47A and 47B are located apart from each other in the directions around the longitudinal axis. The engaging pins 47A and 47B protrude toward the inner peripheral direction from an inner peripheral portion of the rotational operation knob 35. Through holes 48A and 48B are provided in the movable cylindrical member 46 so that these through holes 48A and 48B are located apart from each other in the directions around the longitudinal axis. Each of the through holes 48A and 48B is formed into the shape of a long hole along the longitudinal axis C, and passes through the movable cylindrical member 46 in diametrical directions. The through hole 48A is defined by a hole defining portion 43A, and the through hole 48B is defined by a hole defining portion 43B. The connection cylindrical member 45 is provided with engaging depressions 49A and 49B that are depressed (concaved) toward the inner peripheral direction. The engaging depressions 49A and 49B are provided apart from each other in the directions around the longitudinal axis.

The engaging pin 47A is inserted through the through hole 48A, and is engaged with the engaging depression 49A. The engaging pin 47B is inserted through the through hole 48B, and is engaged with the engaging depression 49B. When each of the engaging pins 47A and 47B engages with the corresponding engaging depression 49A or 49B, the connection cylindrical member 45 is fixed to the rotational operation knob 35. When each of the engaging pins 47A and 47B is inserted through the corresponding through hole 48A or 48B, the movable cylindrical member 46 and the rotational operation knob 35 are regulated in a state that they are unrotatable relative to each other in the directions around the longitudinal axis. However, as each of the through holes 48A and 48B is formed into the shape of a long hole along the longitudinal axis C, the movable cylindrical member 46 is movable relative to the rotational operation knob 35 and the connection cylindrical member 45 along the longitudinal axis C. According to the configuration described above, the connection cylindrical member 45 and the movable cylindrical member 46 are rotatable relative to the cylindrical case 31 together with the rotational operation knob 35 in the directions around the longitudinal axis. Moreover, the movable cylindrical member 46 is movable relative to the probe 3 and the handle unit 4 along the longitudinal axis C.

An elastic member 51 is fixed to the outer peripheral portion of the proximal portion of the probe (see FIG. 3). When the probe 3 is coupled to the horn 15, the elastic member 51 is located at a node position of the ultrasonic vibrations. The elastic member 51 is pressed toward the inner peripheral direction by the inner peripheral portion of the connection cylindrical member 45, and is contracted (compressed). The probe 3 is fixed to the connection cylindrical member 45 by the contraction (compression) of the elastic member 51. As a result, the probe 3 is coupled to the sheath 5 by the connection cylindrical member 45 and the elastic member 51. When the rotational operation knob 35 is rotated in one of the direction around the longitudinal axis, a rotational drive force from the rotational operation knob 35 is transmitted to the probe 3 via the connection cylindrical member 45 and the elastic member 51. Consequently, the probe 3 is rotatable relative to the cylindrical case 31 together with the rotational operation knob 35 and the connection cylindrical member 45.

As shown in FIG. 4, the movable cylindrical member 46 and the vibrator case (oscillator case) 11 are engaged with each other so that the movable cylindrical member 46 is inserted into the vibrator case 11 in a coupling portion of the sheath 5 and the vibrator unit 2. The rotation of the movable cylindrical member 46 and the vibrator case 11 relative to each other in the directions around the longitudinal axis is regulated. However, the movable cylindrical member 46 is movable relative to the vibrator case 11 along the longitudinal axis C.

A connection ring 53 is provided to the outer peripheral direction side of the vibrator case 11 in a coupling portion of the sheath 5 and the vibrator case 11. The connection ring 53 is provided so that the connection ring 53 is fixed to the cylindrical case 31 of the handle unit 4. When the vibrator case 11 is coupled to the sheath 5 (movable cylindrical member 46), the outer peripheral portion of the distal portion of the vibrator case 11 is in contact with the connection ring 53, and the inner peripheral portion of the distal portion of the vibrator case 11 is in contact with the movable cylindrical member 46. The vibrator case 11 and the sheath 5 are rotatable together relative to the connection ring 53 in the directions around the longitudinal axis.

A switch arrangement portion 55 is provided in the fixed handle 32. A first energy mode input button 57A which is a first energy mode input section and a second energy mode input button 57B which is a second energy mode input section are provided in the switch arrangement portion 55. The first energy mode input button 57A and the second energy mode input button 57B are located on the distal face of the fixed handle 32. The first energy mode input button 57A is used to perform an input operation of switching a first energy mode. The second energy mode input button 57B is used to perform an input operation of switching a second energy mode. A first switch portion 58A, a second switch portion 58B, and an electric circuit substrate 59 are provided in the switch arrangement portion 55. The first switch portion 58A is switched on or switched off by the input operation in the first energy mode input button 57A. Similarly, the second switch portion 58B is switched on or switched off by the input operation in the second energy mode input button 57B.

As shown in FIG. 4, the electric circuit substrate 59 is connected to a conductive portion (not shown) of the connection ring 53 via an electric signal line 56. An electric signal line (not shown) which electrically connects a conductive portion (not shown) of the vibrator case 11 and the controller 9 of the power supply unit 7 is provided to the inside of the cable 6. The first switch portion 58A is switched on by the pressing of the first energy mode input button 57A. An electric signal is transmitted to the controller 9 of the power supply unit 7 from the first energy mode input button 57A (first switch portion 58A) through the electric signal line 56, the conductive portion of the connection ring 53, the conductive portion of the vibrator case 11, and the electric signal line extended inside the cable 6. As a result, the first energy mode is set, and an ultrasonic generating current having a predetermined current value is output, for example, from the ultrasonic generating current supplier 8. Similarly, the second switch portion 58B is switched on by the pressing of the second energy mode input button 57B. An electric signal is then transmitted to the controller 9 of the power supply unit 7 from the second energy mode input button 57B (second switch portion 58B) through the electric signal line 56, the conductive portion of the connection ring 53, the conductive portion of the vibrator case 11, and the electric signal line extended inside the cable 6. As a result, the second energy mode is set, and an ultrasonic generating current having a current value smaller than that in the first energy mode is output, for example, from the ultrasonic generating current supplier 8. Therefore, ultrasonic vibrations having an amplitude smaller that in the first energy mode are generated in the second energy mode.

As shown in FIG. 4, the sheath 5 includes a fixed cylindrical member 71 located to the inner peripheral direction side of the rotational operation knob 35. The fixed cylindrical member 71 is fixed to the rotational operation knob 35. A proximal portion of an outer tube 72 and a proximal portion of an outer pipe 73 are fixed to a distal portion of the fixed cylindrical member 71. The outer tube 72 is located to an outer peripheral direction side of the outer pipe 73, and forms an exterior of the sheath 5. An inner tube 75 is provided to the inner peripheral direction side of the outer pipe 73. The inner tube 75 is fixed to the outer pipe 73 via fixing pins 76A and 76B. The configuration described above allows the rotational operation knob 35 to be rotatable relative to the cylindrical case 31 together with the outer tube 72, the outer pipe 73, and the inner tube 75 in the directions around the longitudinal axis.

The sheath 5 includes an inner pipe 77 provided between the outer pipe 73 and the inner tube 75 in the diametrical directions. The inner pipe 77 is fixed to the distal portion of the movable cylindrical member 46 via a connection member 78 and a connection pin 79. The inner pipe 77 is movable relative to the outer tube 72, the outer pipe 73, and the inner tube 75 along the longitudinal axis C together with the movable cylindrical member 46. That is, the inner pipe 77 is movable relative to the handle unit 4 and the probe 3 along the longitudinal axis C together with the movable cylindrical member 46.

As the inner pipe 77 is fixed to the movable cylindrical member 46, a rotational operation in the rotational operation knob 35 is transmitted via the movable cylindrical member 46. Therefore, the inner pipe 77 is rotatable relative to the cylindrical case 31 in the directions around the longitudinal axis together with the rotational operation knob 35. As described above, the rotational operation knob 35 is rotatable relative to the cylindrical case 31 in the directions around the longitudinal axis together with the outer tube 72, the outer pipe 73, and the inner tube 75. Thus, the sheath 5 is rotatable relative to the cylindrical case 31 in the directions around the longitudinal axis together with the rotational operation knob 35.

FIG. 6 is a diagram showing the distal portion of the probe 3, the distal portion of the sheath 5, and the jaw 42. As shown in FIG. 6, the outer tube 72, the outer pipe 73, the inner tube 75, and the inner pipe 77 are extend up to the distal portion of the sheath 5 along the longitudinal axis C. As shown in FIG. 3, a plurality of support members 85 are formed in the outer peripheral portion of the probe 3. The support members 85 are arranged apart from one another in the directions parallel to the longitudinal axis C. When the probe 3 is coupled to the horn 15, each of the support members 85 is located at the node position of the ultrasonic vibrations. The support members 85 support the probe 3 between the probe 3 and the sheath 5. The support members 85 also prevent the contact between the inner tube 75 (sheath 5) and the probe 3.

As shown in FIG. 6, the jaw 42 is attached to the distal portion of the sheath 5 (the distal portion of the outer tube 72 and the distal portion of the outer pipe 73) via a coupling screw 87. The jaw 42 is rotatable relative to the sheath 5 around (about) the coupling screw 87. The distal portion of the inner pipe 77 is coupled to the jaw 42 via a connection pin 89.

FIG. 7 is a sectional view taken along the line VII-VII in FIG. 4. As shown in FIG. 4 and FIG. 7, the movable handle 33 is attached to the cylindrical case 31 via a support pin 91. The movable handle 33 rotates relative to the cylindrical case 31 around (about) the support pin 91. The movable handle 33 includes arms 92A and 92B. The arm 92A is provided with an engaging protrusion 93A protruding toward the inner peripheral direction, and the arm 92B is provided with an engaging protrusion 93B protruding toward the inner peripheral direction.

A slide member 95 is provided to the outer peripheral direction side of the movable cylindrical member 46. In the slide member 95, an engaging groove 96 which is depressed toward the inner peripheral direction is formed along the directions around the longitudinal axis. When the engaging protrusions 93A and 93B engage with the engaging groove 96, the movable handle 33 is attached to the slide member 95. The slide member 95 is rotatable relative to the movable handle 33 and the cylindrical case 31 in the directions around the longitudinal axis together with the movable cylindrical member 46.

A coil spring 97 which is an elastic member and a stopper 98 are provided to the outer peripheral direction side of the movable cylindrical member 46. The coil spring 97 has one end connected to a distal end of the slide member 95, and the other end connected to the movable cylindrical member 46. The movable cylindrical member 46 includes a protrusion 99 protruding toward the outer peripheral direction. The coil spring 97 is connected to the protrusion 99 of the movable cylindrical member 46. The length of the coil spring 97 in its natural state is L0. When the jaw 42 is out of contact with a grasping target, the coil spring 97 is attached between the protrusion 99 of the movable cylindrical member 46 and the slide member 95 in a normal state in which the coil spring 97 has contracted from the natural state by a displacement amount x0. Thus, when the jaw 42 is out of contact with the grasping target, elastic force k0x0 acts on the movable cylindrical member 46 from the coil spring 97 wherein the elastic coefficient of the coil spring 97 is k0. The movement of the slide member 95 toward the proximal direction is regulated by the stopper 98.

When the grasping target is grasped between the probe treatment portion 23 and the jaw 42, a surgeon (operator) presses the movable handle 33 toward the fixed handle 32, and closes the movable handle 33 relative to the fixed handle 32. As a result, the movable handle 33 rotates around the support pin 91, and the slide member 95, the movable cylindrical member 46, and the inner pipe 77 move together toward (in) the distal direction along the longitudinal axis C. In this case, the coil spring 97 does not contract from the normal state, and the elastic force acting on the movable cylindrical member 46 from the coil spring 97 does not change from k0x0. The jaw 42 is closed relative to the probe treatment portion 23 by the movement of the inner pipe 77 toward the distal direction.

When the jaw 42 has come into contact with a grasping target such as a living tissue, the closing of the jaw 42 temporarily stops. Thus, the movement of the movable cylindrical member 46 and the inner pipe 77 toward the distal direction temporarily stops. When the movable handle 33 is further closed relative to the fixed handle 32 in this state, the slide member 95 moves relative to the movable cylindrical member 46 toward the distal direction.

The coil spring 97 further contracts from the normal state in response to the movement of the slide member 95 relative to the movable cylindrical member 46. The elastic force acting on the movable cylindrical member 46 from the coil spring 97 when the coil spring 97 has further contracted from the normal state is k0(x0+x), wherein x is the displacement amount (contraction amount) of the coil spring 97 from the normal state. This elastic force is greater than the elastic force k0x0 in the normal state. As the elastic force k0(x0+x) greater than the elastic force k0x0 in the normal state acts on the movable cylindrical member 46 from the coil spring 97, the movable cylindrical member 46 and the inner pipe 77 that have temporarily stopped further move toward the distal direction. As a result, the jaw 42 which has come into contact with the grasping target is further closed relative to the probe treatment portion 23. Therefore, a grasping force of grasping the grasping target between the jaw 42 and the probe treatment portion 23 is greater than when the coil spring 97 is in the normal state.

As shown in FIG. 4, a torsion spring 101 is attached to the handle unit 4. FIG. 8 is a diagram showing the configuration of attaching the torsion spring 101 to the handle unit 4. As shown in FIG. 8, the torsion spring 101 includes a supporting point portion 102, a first rod 103, and a second rod 105. The supporting point 102 portion is attached to the cylindrical case 31 via a coupling pin 106. The first rod 103 and the second rod 105 are urged to open relative to each other. The first rod 103 is covered with a first thermal contraction tube 108, and the second rod 105 is covered with a second thermal contraction tube 109. The first thermal contraction tube 108 is put in pressure contact with the inner wall located to the distal direction side part of the fixed handle 32 by an urging force acting on the first rod 103. The second thermal contraction tube 109 is put in pressure contact with the movable handle 33 by an urging force acting on the second rod 105. In this way, the torsion spring 101 is attached to the handle unit 4. The movable handle 33 is urged to open relative to the fixed handle 32 by the urging force acting on the first rod 103 and the second rod 105.

When the jaw 42 is opened relative to the probe treatment portion 23 from a condition in which the grasping target is grasped between the jaw 42 and the probe treatment portion 23, the surgeon stops the pressing of the movable handle 33. As a result, the movable handle 33 is opened relative to the fixed handle 32 by the urging force acting on the first rod 103 and the second rod 105. When the movable handle 33 is opened relative to the fixed handle 32, the slide member 95 moves relative to the movable cylindrical member 46 toward the proximal direction. Thus, the coil spring 97 spreads into the normal state. The slide member 95, the movable cylindrical member 46, and the inner pipe 77 then move together toward the proximal direction along the longitudinal axis C. The jaw 42 is opened relative to the probe treatment portion 23 by the movement of the inner pipe 77 toward the proximal direction.

As shown in FIG. 4, the movable handle 33 includes a protrusion 38 protruding toward the proximal direction. The cylindrical case 31 is provided with an abutting portion 39 with which the protrusion 38 comes into abutment when the jaw 42 is open relative to the probe treatment portion 23. The opening of the movable handle 33 relative to the fixed handle 32 is regulated by the abutment of the protrusion 38 on the abutting portion 39. Thus, the protrusion 38 abuts on the abutting portion 39, so that the fixed handle 32 is open relative to the movable handle 33 to the full, and the jaw 42 is open relative to the probe treatment portion 23 to the full.

FIG. 9 is a diagram showing the configuration of coupling the rotational operation knob 35 to the movable cylindrical member 46 when the protrusion 38 is in abutment with the abutting portion 39. As shown in FIG. 9, when the protrusion 38 is in abutment with the abutting portion 39 (when the jaw 42 is open relative to the probe treatment portion 23 to the full), a distal end of the hole defining portion 43A does not abut on the engaging pin 47A, and a distal end of the hole defining portion 43B does not abut on the engaging pin 47B. That is, when the protrusion 38 is in abutment with the abutting portion 39, there is a clearance between the movable cylindrical member 46 and the engaging pins 47A and 47B in the directions parallel to the longitudinal axis C. In this way, the abutment of the distal end of each of the hole defining portions 43A and 43B and the corresponding engaging pin 47A or 47B is prevented when the jaw 42 is open relative to the probe treatment portion 23 to the full. According to this configuration, no frictional force acts between the distal end of the hole defining portion 43A and the engaging pin 47A, and no frictional force acts between the distal end of the hole defining portion 43B and the engaging pin 47B. Therefore, deterioration in the rotational performance of the rotational operation knob 35 caused by the frictional force is effectively prevented when the jaw 42 is open relative to the probe treatment portion 23 to the full. That is, the performance of the rotation of the rotational operation knob 35 relative to the cylindrical case 31 in the directions around the longitudinal axis is ensured, and operability is ensured in the rotational operation in the rotational operation knob 35.

Figure 12:
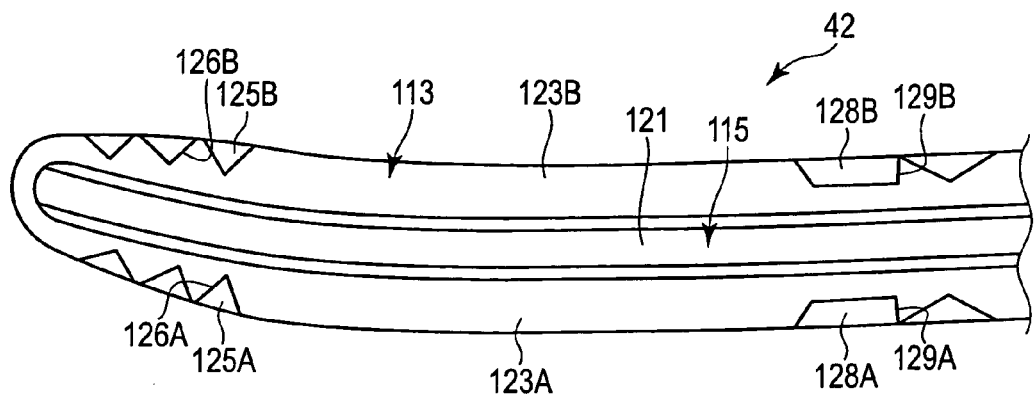
FIG. 12 is a schematic diagram showing the configuration of the jaw according to the first embodiment viewed from a side of a probe treatment portion.
Figure 13:
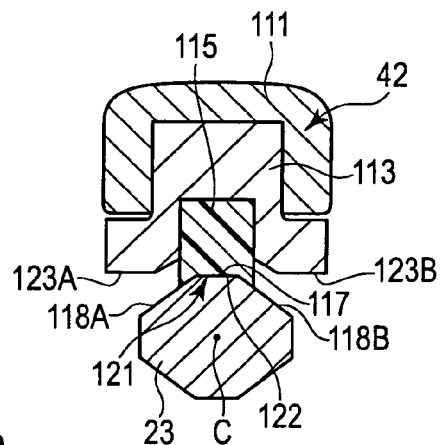
FIG. 13 is a sectional view taken along the line 13-13 in FIG. 6.
Figure 14:
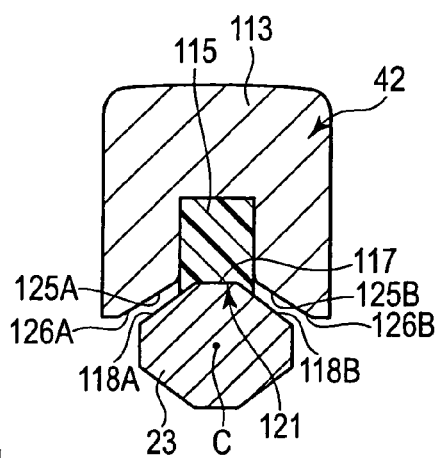
FIG. 14 is a sectional view taken along the line 14-14 in FIG. 6.

FIG. 10 to FIG. 12 are diagrams showing the configuration of the jaw 42. FIG. 13 is a sectional view taken along the line 13-13 in FIG. 6. FIG. 14 is a sectional view taken along the line 14-14 in FIG. 6. As shown in FIG. 10 to FIG. 14, the jaw 42 includes a jaw body 111 attached to the sheath 5. A metallic member 113 is coupled to the jaw body 111 via a connection pin 112. A pad member 115 which is an abutting member is attached to the metallic member 113. The pad member 115 is made of an insulating material such as a resin.

As shown in FIG. 13 and FIG. 14, the probe treatment portion 23 includes a probe perpendicularly facing surface 117 which is perpendicular to the opening-and-closing directions of the jaw 42. The probe perpendicularly facing surface 117 faces the jaw 42. Probe obliquely facing surfaces 118A and 118B are formed by the probe treatment portion 23 on both sides of the probe perpendicularly facing surface 117 in width directions, the width directions being directions perpendicular to the longitudinal axis C and perpendicular to the opening-and-closing directions of the jaw 42.

An abutting portion 121 is formed in the jaw 42 by the pad member 115. The surface of the abutting portion 121 is formed into a planar shape that is not uneven. When the jaw 42 is closed relative to the probe treatment portion 23 while a grasping target such as a blood vessel or a membranous tissue is not located between the probe treatment portion 23 and the jaw 42, the abutting portion 121 comes into abutment with the probe perpendicularly facing surface 117 and the probe obliquely facing surfaces 118A and 118B of the probe treatment portion 23. That is, the abutting portion 121 is abutable on the probe treatment portion 23 when the jaw 42 is closed relative to the probe treatment portion 23. The abutting portion 121 includes a jaw perpendicularly facing surface 122 which is perpendicular to the opening-and-closing directions of the jaw 42. The jaw perpendicularly facing surface 122 is parallel to the probe perpendicularly facing surface 117. The jaw perpendicularly facing surface 122 is abutable on the probe perpendicularly facing surface 117 while the jaw 42 is closed relative to the probe treatment portion 23.

Separated portions 123A and 123B are formed by the metallic member 113 on both sides of the abutting portion 121 in the jaw 42 in the width directions, which are the directions perpendicular to the longitudinal axis C and perpendicular to the opening-and-closing directions of the jaw 42. As shown in FIG. 10 to FIG. 12, the separated portions 123A and 123B are located in a intermediate part of the jaw 42 in the directions parallel to the longitudinal axis C. As shown in FIG. 13, a clearance is always formed between the probe obliquely facing surface 118A and the separated portion 123A and between the probe obliquely facing surface 118B and the separated portion 123B when the jaw 42 is closed relative to the probe treatment portion 23. That is, the separated portions 123A and 123B are disposed with the clearance between the separated portions 123A and 123B and the probe treatment portion 23 when the abutting portion 121 (pad member 115) is in abutment with the probe treatment portion 23.

As shown in FIG. 10 to FIG. 12, the jaw 42 is provided with distal-side wall portions 125A and 125B to the distal direction side of the separated portions 123A and 123B. The distal-side wall portions 125A and 125B are formed by the metallic member 113. As shown in FIG. 14, the distal-side wall portions 125A and 125B are located on both sides of the abutting portion 121 in the jaw 42 in the width directions, which are the directions perpendicular to the longitudinal axis C and perpendicular to the opening-and-closing directions of the jaw 42. The distal-side wall portions 125A and 125B protrude toward the probe treatment portion 23 as compared with the separated portions 123A and 123B. Thus, a clearance between the distal-side wall portions 125A and 125B and the probe treatment portion 23 is smaller than the clearance between the separated portions 123A and 123B and the probe treatment portion 23. The distal-side wall portion 125A includes a distal tooth portion 126A. The distal-side wall portion 125B includes a distal tooth portion 126B. Surfaces of the distal tooth portions 126A and 126B facing toward a closing direction of the jaw 42 are formed into an uneven shape along the longitudinal axis C.

As shown in FIG. 10 to FIG. 12, the jaw 42 includes proximal-side wall portions 128A and 128B provided to the proximal direction side of the separated portions 123A and 123B. The proximal-side wall portions 128A and 128B are formed by the metallic member 113. The proximal-side wall portions 128A and 128B are located on both sides of the abutting portion 121 in the jaw 42 in the width directions, which are the directions perpendicular to the longitudinal axis C and perpendicular to the opening-and-closing directions of the jaw 42. As the distal-side wall portions 125A and 125B, the proximal-side wall portions 128A and 128B protrude toward the probe treatment portion 23 as compared with the separated portions 123A and 123B. Thus, a clearance between the proximal-side wall portions 128A and 128B and the probe treatment portion 23 is smaller than the clearance between the separated portions 123A and 123B and the probe treatment portion 23. The proximal-side wall portion 128A includes a proximal tooth portion 129A. The proximal-side wall portion 128B includes a proximal tooth portion 129B. Surfaces of the proximal tooth portions 129A and 129B facing toward the closing direction of the jaw 42 are formed into an uneven shape along the longitudinal axis C.

Figure 15:
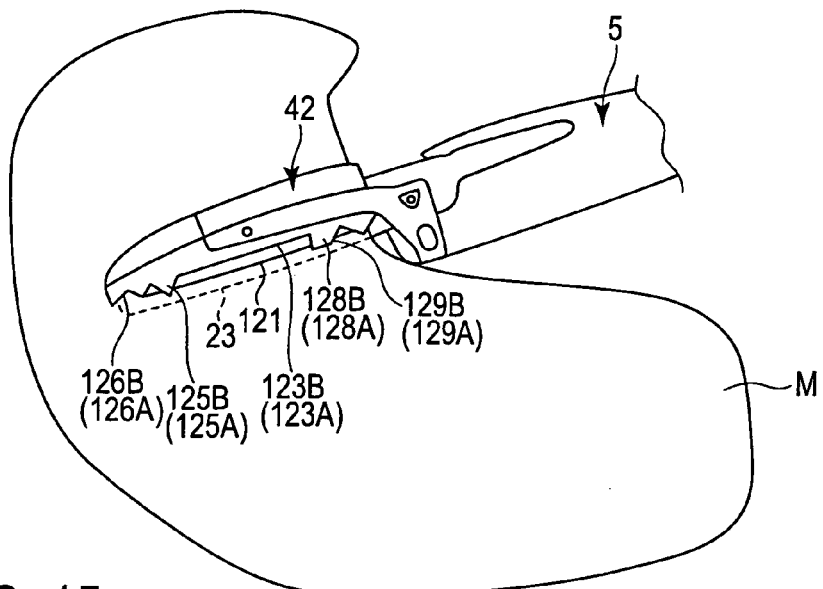
FIG. 15 is a schematic diagram showing a state in which a membranous tissue is grasped between the probe treatment portion and the jaw according to the first embodiment.

Now, the functions of the grasping treatment device 1 according to the present embodiment are described. The grasping treatment device 1 is mainly used in the cutting and coagulation of a membranous tissue such as a mesentery or a gastric membrane. FIG. 15 is a diagram showing a state in which a membranous tissue M is grasped as a grasping target between the jaw 42 and the probe treatment portion 23. As shown in FIG. 15, when the membranous tissue M is grasped between the jaw 42 and the probe treatment portion 23, the jaw 42 is in contact with the membranous tissue M over an entire length in the directions parallel to the longitudinal axis C.

In this condition, the first energy mode input button 57A or the second energy mode input button 57B is pressed. As a result, an electric signal is transmitted to the controller 9 of the power supply unit 7 from the first switch portion 58A or the second switch portion 58B. An ultrasonic generating current is then output from the ultrasonic generating current supplier 8, and ultrasonic vibrations are generated in the ultrasonic vibrator 12. The probe 3 then vibrates in the directions parallel to the longitudinal axis C, and the ultrasonic vibrations are transmitted to the probe treatment portion 23. The membranous tissue M as the grasping target grasped between the probe treatment portion 23 and the jaw 42 is cut and coagulated by frictional heat generated by the ultrasonic vibrations of the probe treatment portion 23. That is, the probe treatment portion 23 serves as an ultrasonic treatment portion which uses the transmitted ultrasonic vibrations to treat the membranous tissue M as the grasping target.

Here, the jaw 42 is provided with the distal tooth portions 126A and 126B and the proximal tooth portions 129A and 129B in which surfaces facing toward the closing direction of the jaw 42 are formed into an uneven shape along the longitudinal axis C. Thus, when the membranous tissue M is grasped between the jaw 42 and the probe treatment portion 23, the membranous tissue M is caught by the distal tooth portions 126A and 126B and the proximal tooth portions 129A and 129B. This ensures that the movement of the membranous tissue M in the directions parallel to the longitudinal axis C is prevented. Therefore, when the membranous tissue M is cut and coagulated, deterioration of treatment performance caused by the movement of the membranous tissue M is effectively prevented.

Figure 16:
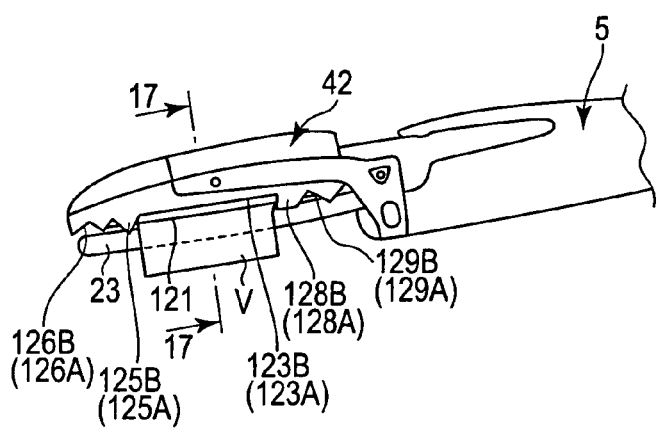
FIG. 16 is a schematic diagram showing a state in which a blood vessel is grasped between the probe treatment portion and the jaw according to the first embodiment.
Figure 17:
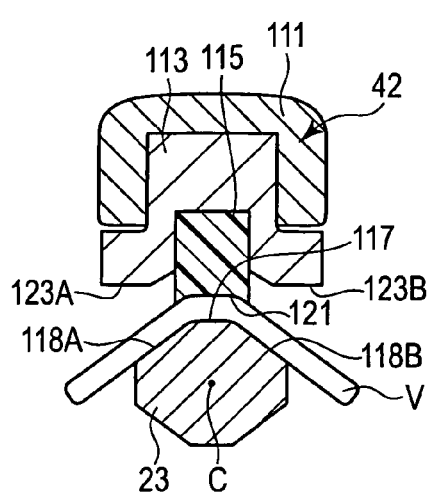
FIG. 17 is a sectional view taken along the line 17-17 in FIG. 16.

During the use of the grasping treatment device 1, the cutting and coagulation of a thick blood vessel having a diameter of about 5 mm may be needed in addition to the cutting and coagulation of the membranous tissue. FIG. 16 is a diagram showing a state in which a blood vessel V is grasped as a grasping target between the jaw 42 and the probe treatment portion 23. FIG. 17 is a sectional view taken along the line 17-17 in FIG. 16. When the thick blood vessel V is cut and coagulated, the sealing performance needs to be higher than when the membranous tissue M is cut and coagulated. Thus, as shown in FIG. 16 and FIG. 17, the blood vessel V is grasped between the abutting portion 121 of the jaw 42 and the probe treatment portion 23, and the planar-shaped abutting portion 121 having the surface that is not uneven is brought in contact with the blood vessel V as the grasping target.

In this condition, ultrasonic vibrations are generated in the ultrasonic vibrator 12, as in the case of the cutting and coagulation of the membranous tissue M. The probe 3 then vibrates in the directions parallel to the longitudinal axis C, and the ultrasonic vibrations are transmitted to the probe treatment portion 23. The blood vessel V as the grasping target grasped between the probe treatment portion 23 and the jaw 42 is cut and coagulated by frictional heat generated by the ultrasonic vibrations of the probe treatment portion 23. That is, the probe treatment portion 23 serves as an ultrasonic treatment portion which uses the transmitted ultrasonic vibrations to treat the blood vessel V as the grasping target.

When the blood vessel V is grasped between the abutting portion 121 of the jaw 42 and the probe treatment portion 23, the abutting portion 121 of the jaw 42 having a planar-shaped surface is in contact with the blood vessel V. The probe perpendicularly facing surface 117 and the probe obliquely facing surfaces 118A and 118B having the planar-shaped surfaces are also in contact with the blood vessel V. As the blood vessel V is grasped between the abutting portion 121 having the planar-shaped surface and the probe perpendicularly facing surface 117 and the probe obliquely facing surfaces 118A and 118B having planar-shaped surfaces, the blood vessel V is grasped with a sufficient degree of grasping force. Thus, the blood vessel V is efficiently sealed when the blood vessel V grasped between the abutting portion 121 of the jaw 42 and the probe treatment portion 23 is cut and coagulated.

In the jaw 42, the clearance is formed between the separated portions 123A and 123B and the probe treatment portion 23 when the abutting portion 121 (pad member 115) is in abutment with the probe treatment portion 23. Thus, as shown in FIG. 17, the separated portions 123A and 123B are out of contact with the blood vessel V when the blood vessel V is grasped between the abutting portion 121 of the jaw 42 and the probe treatment portion 23. Therefore, when the blood vessel V is grasped between the abutting portion 121 of the jaw 42 and the probe treatment portion 23, a press force exerted on the blood vessel V from the jaw 42 only acts from the abutting portion 121 and does not act from the separated portions 123A and 123B. That is, the press force exerted on the blood vessel V from the jaw 42 is not dispersed all over the abutting portion 121 and the separated portions 123A and 123B, but concentrates on the abutting portion 121. Therefore, the grasping force to grasp the blood vessel V between the abutting portion 121 and the probe treatment portion 23 is greater. Thus, the blood vessel V is more efficiently sealed when the blood vessel V grasped between the abutting portion 121 of the jaw 42 and the probe treatment portion 23 is cut and coagulated.

The probe perpendicularly facing surface 117 of the probe treatment portion 23 to which the jaw 42 faces is perpendicular to the opening-and-closing directions of the jaw 42. The jaw perpendicularly facing surface 122 of the abutting portion 121 is parallel to the probe perpendicularly facing surface 117 and is abutable on the probe perpendicularly facing surface 117. As shown in FIG. 17, when the blood vessel V is grasped between the abutting portion 121 and the probe treatment portion 23, a large part of the blood vessel V is located between the probe perpendicularly facing surface 117 and the jaw perpendicularly facing surface 122. As the probe perpendicularly facing surface 117 and the jaw perpendicularly facing surface 122 are perpendicular to the opening-and-closing directions of the jaw 42, a grasping force to grasp the blood vessel V as the grasping target is further increased if the large part of the blood vessel V is located between the probe perpendicularly facing surface 117 and the jaw perpendicularly facing surface 122. Thus, the blood vessel V is more efficiently sealed when the blood vessel V grasped between the abutting portion 121 of the jaw 42 and the probe treatment portion 23 is cut and coagulated.

However, when the blood vessel V is grasped between the abutting portion 121 of the jaw 42 and the probe treatment portion 23, the planar-shaped abutting portion 121 having the surface that is not uneven contacts the blood vessel V in the jaw 42, and the planar-shaped probe perpendicularly facing surface 117 and probe obliquely facing surfaces 118A and 118B having the surfaces that are not uneven contact the blood vessel V in the probe treatment portion 23. Thus, the grasped blood vessel V is apt to move in the directions parallel to the longitudinal axis C. For example, when the blood vessel V is grasped so that the distal direction substantially corresponds to a vertically downward direction, the blood vessel V is apt to be moved by gravitation toward the distal direction substantially corresponding to the vertically downward direction. In contrast, when the blood vessel V is grasped so that the distal direction substantially corresponds to a vertically upward direction, the blood vessel V is apt to be moved by gravitation toward the proximal direction substantially corresponding to the vertically downward direction. When the blood vessel V grasped between the abutting portion 121 of the jaw 42 and the probe treatment portion 23 is cut and coagulated, the probe treatment portion 23 (probe 3) is vibrating in the directions parallel to the longitudinal axis C. Thus, the blood vessel V is more apt to move in the directions parallel to the longitudinal axis C owing to the ultrasonic vibrations.

Accordingly, in the jaw 42 according to the present embodiment, the distal-side wall portions 125A and 125B protruding toward the probe treatment portion 23 as compared with the separated portions 123A and 123B are provided to the distal direction side of the separated portions 123A and 123B. As shown in FIG. 16, when the blood vessel V is grasped between the abutting portion 121 of the jaw 42 and the probe treatment portion 23, the blood vessel V is in abutment with proximal ends of the distal-side wall portions 125A and 125B. The movement of the blood vessel V as the grasping target toward the distal direction away from the separated portions 123A and 123B is regulated by the abutment of the blood vessel V on the distal-side wall portions 125A and 125B.

Moreover, in the jaw 42, the proximal-side wall portions 128A and 128B protruding toward the probe treatment portion 23 as compared with the separated portions 123A and 123B are provided to the proximal direction side of the separated portions 123A and 123B. As shown in FIG. 16, when the blood vessel V is grasped between the abutting portion 121 of the jaw 42 and the probe treatment portion 23, the blood vessel V is in abutment with distal ends of the proximal-side wall portions 128A and 128B. The movement of the grasping target blood vessel V toward the proximal direction away from the separated portions 123A and 123B is regulated by the abutment of the blood vessel V on the proximal-side wall portions 128A and 128B.

In this way, the distal-side wall portions 125A and 125B and the proximal-side wall portions 128A and 128B prevent the blood vessel V grasped between the abutting portion 121 of the jaw 42 and the probe treatment portion 23 from moving in the directions parallel to the longitudinal axis C. The prevention of the movement of the blood vessel V as the grasping target in the directions parallel to the longitudinal axis C is ensured, so that deterioration of treatment performance caused by the movement of the blood vessel V is effectively prevented when the blood vessel V is cut and coagulated.

Accordingly, the grasping treatment device 1 having the configuration described above has the following advantageous effects. In the grasping treatment device 1, when the blood vessel V is grasped between the abutting portion 121 of the jaw 42 and the probe treatment portion 23, the abutting portion 121 of the jaw 42 having the planar-shaped surface is in contact with the blood vessel V. As the blood vessel V is grasped between the abutting portion 121 having the planar-shaped surface and the probe treatment portion 23, the blood vessel V is grasped with a sufficient degree of grasping force. Thus, the blood vessel V as the grasping target can be efficiently sealed when the blood vessel V grasped between the abutting portion 121 of the jaw 42 and the probe treatment portion 23 is cut and coagulated.

In the jaw 42 of the grasping treatment device 1, there is a clearance between the separated portions 123A and 123B and the probe treatment portion 23 when the abutting portion 121 (pad member 115) is in abutment with the probe treatment portion 23. Thus, the separated portions 123A and 123B are out of contact with the blood vessel V when the blood vessel V is grasped between the abutting portion 121 of the jaw 42 and the probe treatment portion 23. Therefore, when the blood vessel V is grasped between the abutting portion 121 of the jaw 42 and the probe treatment portion 23, a press force exerted on the blood vessel V from the jaw 42 only acts from the abutting portion 121 and does not act from the separated portions 123A and 123B. That is, the press force exerted on the blood vessel V from the jaw 42 is not dispersed all over the abutting portion 121 and the separated portions 123A and 123B, but concentrates on the abutting portion 121. Therefore, the grasping force to grasp the blood vessel V between the abutting portion 121 and the probe treatment portion 23 is greater. Thus, the blood vessel V can be more efficiently sealed when the blood vessel V grasped between the abutting portion 121 of the jaw 42 and the probe treatment portion 23 is cut and coagulated.

Furthermore, in the grasping treatment device 1, when the blood vessel V is grasped between the abutting portion 121 of the jaw 42 and the probe treatment portion 23, the blood vessel V is in abutment with the proximal ends of the distal-side wall portions 125A and 125B and the distal ends of the proximal-side wall portions 128A and 128B. The movement of the blood vessel V as the grasping target toward the distal direction away from the separated portions 123A and 123B is regulated by the abutment of the blood vessel V on the distal-side wall portions 125A and 125B. The movement of the blood vessel V of the grasping target toward the proximal direction away from the separated portions 123A and 123B is regulated by the abutment of the blood vessel V on the proximal-side wall portions 128A and 128B. That is, the distal-side wall portions 125A and 125B and the proximal-side wall portions 128A and 128B prevent the blood vessel V grasped between the abutting portion 121 of the jaw 42 and the probe treatment portion 23 from moving in the directions parallel to the longitudinal axis C. The prevention of the movement of the blood vessel V as the grasping target in the directions parallel to the longitudinal axis C is thus ensured, so that deterioration of treatment performance caused by the movement of the blood vessel V can be effectively prevented when the blood vessel V is cut and coagulated.

(Modifications)

Although the distal tooth portions 126A and 126B and the proximal tooth portions 129A and 129B are provided in the first embodiment, this is not a limitation. For example, as in a first modification shown in FIG. 18, no distal tooth portions 126A and 126B and no proximal tooth portions 129A and 129B may be provided. In the present modification as well, the distal-side wall portions 125A and 125B protruding toward the probe treatment portion 23 as compared with the separated portions 123A and 123B are provided to the distal direction side of the separated portions 123A and 123B, as in the first embodiment. The proximal-side wall portions 128A and 128B protruding toward the probe treatment portion 23 as compared with the separated portions 123A and 123B are provided to the proximal direction side of the separated portions 123A and 123B. The distal-side wall portions 125A and 125B and the proximal-side wall portions 128A and 128B prevent the blood vessel V grasped between the abutting portion 121 of the jaw 42 and the probe treatment portion 23 from moving in the directions parallel to the longitudinal axis C. However, in the present modification, the distal tooth portions 126A and 126B and the proximal tooth portions 129A and 129B are not provided, so that the membranous tissue M grasped between the jaw 42 and the probe treatment portion 23 is more apt to move in the directions parallel to the longitudinal axis C than in the first embodiment.

The distal tooth portions 126A and 126B may be only provided in the distal-side wall portions 125A and 125B, and no proximal tooth portions 129A and 129B may be provided in the proximal-side wall portions 128A and 128B. The proximal tooth 129A and 129B may be only provided in the proximal-side wall portions 128A and 128B, and no distal tooth 126A and 126B may be provided in the distal-side wall portions 125A and 125B.

In the first embodiment, the abutting portion 121 of the jaw 42 includes the jaw perpendicularly facing surface 122 perpendicular to the opening-and-closing directions of the jaw 42. The abutting portion 121 is provided to a intermediate part of the jaw 42 in the width directions, which are the directions perpendicular to the longitudinal axis C and perpendicular to the opening-and-closing directions of the jaw 42. However, for example, as in a second modification shown in FIG. 19 and FIG. 20, the abutting portion 121 may be formed by the pad member 115 in one end part of the jaw 42 in the width directions which are directions perpendicular to the longitudinal axis C and perpendicular to the opening-and-closing directions of the jaw 42. In the present modification, the abutting portion 121 includes a jaw obliquely facing surface 131. The jaw obliquely facing surface 131 is parallel to the probe obliquely facing surface 118A. The jaw obliquely facing surface 131 is abutable on the probe obliquely facing surface 118A while the jaw 42 is closed relative to the probe treatment portion 23.

In the present modification, the separated portions 123A and 123B are formed by the metallic member 113 in the intermediate part of the jaw 42 in the directions parallel to the longitudinal axis C, as in the first embodiment. However, in the present modification, the abutting portion 121 is located on one side of the separated portion 123A in the width directions which are the directions perpendicular to the longitudinal axis C and perpendicular to the opening-and-closing directions of the jaw 42. The separated portion 123B is located on the other side of the separated portion 123A in the width directions which are the directions perpendicular to the longitudinal axis C and perpendicular to the opening-and-closing directions of the jaw 42. As shown in FIG. 19, a clearance is always formed between the probe perpendicularly facing surface 117 and the separated portion 123A and between the probe obliquely facing surface 118B and the separated portion 123B when the jaw 42 is closed relative to the probe treatment portion 23. That is, the separated portions 123A and 123B are disposed with the clearance between the separated portions 123A and 123B and the probe treatment portion 23 when the abutting portion 121 (pad member 115) is in abutment with the probe treatment portion 23.

In the present modification, in the jaw 42, the distal-side wall portions 125A and 125B are formed by the metallic member 113 to the distal direction side of the separated portion 123A and 123B, as in the first embodiment. The proximal-side wall portions 128A and 128B are formed by the metallic member 113 to the proximal direction side of the separated portions 123A and 123B. As shown in FIG. 20, the distal-side wall portions 125A and 125B protrude toward the probe treatment portion 23 as compared with the separated portions 123A and 123B. Therefore, in the present modification, the movement of the blood vessel V as the grasping target toward the distal direction away from the separated portions 123A and 123B is regulated by the distal-side wall portions 125A and 125B when the blood vessel V is grasped between the abutting portion 121 of the jaw 42 and the probe treatment portion 23, as in the first embodiment. Similarly, the proximal-side wall portions 128A and 128B protrude toward the probe treatment portion 23 as compared with the separated portions 123A and 123B. Therefore, in the present modification, the movement of the blood vessel V as the grasping target toward the proximal direction away from the separated portions 123A and 123B is regulated by the proximal-side wall portions 128A and 128B when the blood vessel V is grasped between the abutting portion 121 of the jaw 42 and the probe treatment portion 23, as in the first embodiment.

However, in the present modification, the abutting portion 121 of the jaw 42 does not include a surface perpendicular to the opening-and-closing directions of the jaw 42. The abutting portion 121 of the jaw 42 does not abut on the probe perpendicularly facing surface 117 of the probe treatment portion 23 perpendicular to the opening-and-closing directions of the jaw 42. Therefore, in the present modification, the grasping force to grasp the blood vessel V between the abutting portion 121 of the jaw 42 and the probe treatment portion 23 is smaller than in the first embodiment.

In the first embodiment, the distal-side wall portions 125A and 125B are located on both sides of the abutting portion 121 in the width directions which are the directions perpendicular to the longitudinal axis C and perpendicular to the opening-and-closing directions of the jaw 42. The proximal-side wall portions 128A and 128B are located on both sides of the abutting portion 121 in the width directions which are the directions perpendicular to the longitudinal axis C and perpendicular to the opening-and-closing directions of the jaw 42. However, for example, as in a third modification shown in FIG. 21, the distal-side wall portion 125 and the proximal-side wall portion 128 may be provided over an entire length (dimension) of the jaw 42 in the width directions. In the present modification, the distal tooth portion 126 is provided in the distal-side wall portion 125, and the proximal tooth portion 129 is provided in the proximal-side wall portion 128. As in the distal tooth portions 126A and 126B and the proximal tooth portions 129A and 129B according to the first embodiment, uneven surfaces facing in the closing direction of the jaw 42 are formed along the longitudinal axis C in the distal tooth portion 126 and the proximal tooth portion 129.

As shown in FIG. 21, in the present modification, the position of a distal end of the abutting portion 121 substantially corresponds to the position of distal ends of the separated portions 123A and 123B in the directions parallel to the longitudinal axis C. The position of a proximal end of the abutting portion 121 substantially corresponds to the position of proximal ends of the separated portions 123A and 123B in the directions parallel to the longitudinal axis C.

In the present modification, in the jaw 42, the distal-side wall portion 125 is located to the distal direction side of the separated portions 123A and 123B, as in the first embodiment. The proximal-side wall portion 128 is located to the proximal direction side of the separated portions 123A and 123B. The distal-side wall portion 125 protrudes toward the probe treatment portion 23 as compared with the separated portions 123A and 123B. Therefore, in the present modification, the movement of the blood vessel V as the grasping target toward the distal direction away from the separated portions 123A and 123B is regulated by the distal-side wall portion 125 when the blood vessel V is grasped between the abutting portion 121 of the jaw 42 and the probe treatment portion 23, as in the first embodiment. Similarly, the proximal-side wall portion 128 protrudes toward the probe treatment portion 23 as compared with the separated portions 123A and 123B. Therefore, in the present modification, the movement of the blood vessel V as the grasping target toward the proximal direction away from the separated portions 123A and 123B is regulated by the proximal-side wall portion 128 when the blood vessel V is grasped between the abutting portion 121 of the jaw 42 and the probe treatment portion 23, as in the first embodiment.

The first to third modifications described above show that the jaw 42 has only to be provided with the abutting portion 121 which is abutable on the probe treatment portion 23 when the jaw 42 is closed relative to the probe treatment portion 23, and the separated portions 123A and 123B which are disposed with the clearance between the separated portions 123A and 123B and the probe treatment portion 23 when the abutting portion 121 is in abutment with the probe treatment portion 23. The distal-side wall portions (125A, 125B, 125) protruding toward the probe treatment portion 23 as compared with the separated portions 123A and 123B have only to be provided to the distal direction side of the separated portions 123A and 123B of the jaw 42. The proximal-side wall portions (128A, 128B, 128) protruding toward the probe treatment portion 23 as compared with the separated portions 123A and 123B have only to be provided to the proximal direction side of the separated portions 123A and 123B of the jaw 42. Thus, the distal-side wall portions (125A, 125B, 125) regulate the movement of the grasping target (V) toward the distal direction away from the separated portions 123A and 123B, and the proximal-side wall portions (128A, 128B, 128) regulate the movement of the grasping target (V) toward the proximal direction away from the separated portions 123A and 123B.

Although the probe 3 is an ultrasonic probe which can transmit ultrasonic vibrations from the proximal direction to the distal direction in the first embodiment, this is not a limitation. For example, as in a fourth modification, the probe 3 may transmit a high-frequency current to the probe treatment portion 23 instead of the ultrasonic vibrations. When the high-frequency current is transmitted to the probe treatment portion 23 through the probe 3, the probe treatment portion 23 serves as a first electrode portion having a first electric potential E1. In the present modification, the connection cylindrical member 45, the elastic member 51, the inner tube 75, and the support members 85 are made of an insulating material, and the probe 3 is electrically insulated from the sheath 5.

As shown in FIG. 22, in the present modification, the jaw 42 includes the abutting portion 121, as in the first embodiment. The abutting portion 121 is provided with the jaw perpendicularly facing surface 122 which is abutable on the probe perpendicularly facing surface 117 when the jaw 42 is closed relative to the probe treatment portion 23. However, in the present modification, the jaw 42 does not include the pad member 115, and the abutting portion 121 is formed by the metallic member 113.

In the present modification, a high-frequency current is transmitted to the metallic member 113 through the movable cylindrical member 46, the inner pipe 77, and the jaw body 111. When the high-frequency current is transmitted to metallic member 113 through the sheath 5, the metallic member 113 serves as a second electrode portion having a second electric potential E2 different from the first electric potential E1. The probe treatment portion 23 has the first electric potential E1, and the metallic member 113 of the jaw 42 has the second electric potential E2, so that the high-frequency current flows through the grasping target grasped between the probe treatment portion 23 and the jaw 42. As a result, a grasping target such as a blood vessel is reformed and coagulated.

As a modification, an ultrasonic probe (3) capable of transmitting ultrasonic vibrations may transmit the high-frequency current to the probe treatment portion 23. In the present modification, when the high-frequency current is transmitted to the probe treatment portion 23 through the probe 3, the probe treatment portion 23 serves as the first electrode portion, as in the first embodiment. The present modification is similar to the first embodiment in the configuration of the jaw 42 except that the high-frequency current is transmitted to the metallic member 113. As in the fourth modification, when the high-frequency current is transmitted to metallic member 113 through the sheath 5, the metallic member 113 serves as the second electrode portion. According to the configuration described above, in the present modification, a grasping target such as a blood vessel grasped between the probe treatment portion 23 and the jaw 42 can be treated by ultrasonic waves and the high-frequency current.

In an alternative modification, a heater (not shown) is provided in at least one of the probe treatment portion 23 and the jaw 42. A grasping target such as a blood vessel grasped between the probe treatment portion 23 and the jaw 42 is treated by heat from the heater.

As described above, the grasping treatment device 1 has only to grasp a grasping target such as a blood vessel or a membranous tissue between the probe treatment portion 23 and the jaw 42, and treat the grasping target by using energy such as ultrasonic vibrations or a high-frequency current.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment device comprising:
a probe having a distal end and a proximal end, and extending along a longitudinal axis;
a jaw configured to open or close relative to the probe, and including an opposed surface that faces toward a closing direction of the jaw and that is opposed to a distal portion of the probe,
the opposed surface including an abutting surface, a distal separated surface, an intermediate separated surface, and a proximal separated surface,
the distal separated surface, the intermediate separated surface, and the proximal separated surface being continuously arranged along the longitudinal axis,
the abutting surface being configured to abut the probe continuously from a proximal end of the abutting surface to a distal end of the abutting surface along the longitudinal axis when the jaw is closed relative to the probe,
the distal separated surface, the intermediate separated surface, and the proximal separated surface being configured to form a clearance between the jaw and the probe such that the clearance continuously extends from a distal end of the distal separated surface to a proximal end of the proximal separated surface along the longitudinal axis when the abutting surface abuts the probe,
the intermediate separated surface being configured to grasp a blood vessel, and
the intermediate separated surface extending from the abutting surface to a first outer edge of the jaw and from the abutting surface to a second outer edge of the jaw along the entire length of the jaw in an intermediate portion of the jaw, the first outer edge of the jaw being on an opposite side of the jaw from the second outer edge of the jaw,
wherein:
the intermediate separated surface and the abutting surface are continuously arranged in a direction perpendicular to a plane of a direction of motion of the jaw,
each of the distal separated surface, the intermediate separated surface, and the proximal separated surface continuously extends to both the first outer edge of the jaw and the second outer edge of the jaw in the direction perpendicular to the plane of the motion of the jaw,
a length of the intermediate separated surface in a direction along the longitudinal axis is longer than a length of each of the distal separated surface and the proximal separated surface in the direction along the longitudinal axis,
a part of the distal separated surface and a part of the proximal separated surface protrude further toward the probe compared with the intermediate separated surface,
the opposed surface includes a distal stepped surface provided at a boundary between a distal end of the intermediate separated surface and a proximal end of the distal separated surface and facing toward a proximal side, and a proximal stepped surface provided at a boundary between a proximal end of the intermediate separated surface and a distal end of the proximal separated surface and facing toward a distal side, and
the distal stepped surface and the proximal stepped surface are configured to regulate a movement of the grasped blood vessel.

2. The grasping treatment device according to claim 1, wherein the probe is configured to receive ultrasonic vibrations, and configured to transmit the ultrasonic vibrations from the proximal end to the distal end.

3. The grasping treatment device according to claim 2, wherein the clearance between the probe and the jaw in the distal separated surface and the proximal separated surface is smaller than the clearance between the probe and the jaw in the intermediate separated surface.

4. The grasping treatment device according to claim 1, wherein an entirety of the intermediate separated surface forms a flat surface extending along the longitudinal axis.

5. The grasping treatment device according to claim 1, wherein the probe is configured to flow a high-frequency current.

6. The grasping treatment device according to claim 1, wherein the jaw includes an electrode portion configured to receive a high-frequency current.

7. The grasping treatment device according to claim 1, wherein the jaw includes a metallic member that forms the distal separated surface, the intermediate separated surface, and the proximal separated surface.

8. The grasping treatment device according to claim 7, wherein the jaw includes an abutting member that is made of resin and that forms the abutting surface.

* * * * *